United States Patent [19]

Kamdar et al.

[11] Patent Number: 6,165,173
[45] Date of Patent: Dec. 26, 2000

[54] MEMORY FOR REGULATING DEVICE UTILIZATION AND BEHAVIOR

[75] Inventors: Kirti P. Kamdar, Sunnyvale; Robin Bek, Campbell, both of Calif.

[73] Assignee: Somnus Medical Technologies, Inc., Sunnyvale, Calif.

[21] Appl. No.: 09/167,222

[22] Filed: Oct. 6, 1998

Related U.S. Application Data

[60] Provisional application No. 60/061,197, Oct. 6, 1997, provisional application No. 60/062,458, Oct. 6, 1997, provisional application No. 60/061,193, Oct. 6, 1997, provisional application No. 60/061,714, Oct. 6, 1997, provisional application No. 60/062,543, Oct. 6, 1997, and provisional application No. 60/061,213, Oct. 6, 1997.

[51] Int. Cl.[7] .................................................... A61B 18/12
[52] U.S. Cl. ............................................. 606/34; 606/41
[58] Field of Search .................................. 606/34, 37–40, 606/41, 12

[56] References Cited

U.S. PATENT DOCUMENTS 4,580,557  4/1986  Hertzmann ................................ 606/12
5,233,515  8/1993  Cosman ............................. 364/413.02

FOREIGN PATENT DOCUMENTS

WO 97/20510  6/1997  WIPO ............................ A61B 17/39

*Primary Examiner*—Lee Cohen
*Attorney, Agent, or Firm*—Wilson Sonsini Goodrich & Rosati

[57] ABSTRACT

A cell necrosis apparatus is described. The cell necrosis apparatus includes an identification and usage device capable of performing an encrypted handshake protocol with an energy source. The identification and usage device is capable of identifying the cell necrosis apparatus, to prevent the use of unauthorized devices with the energy source, as well as controlling and causing a record to be made of a usage of the cell necrosis apparatus.

20 Claims, 9 Drawing Sheets

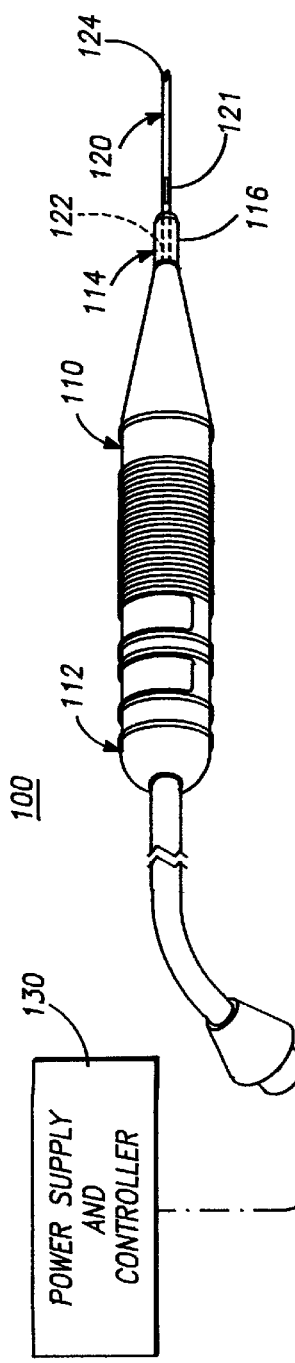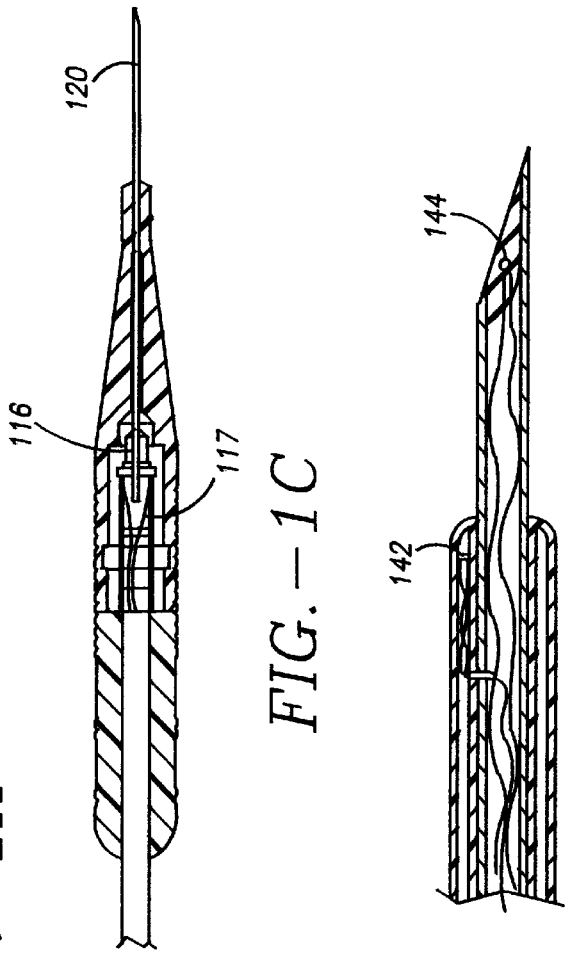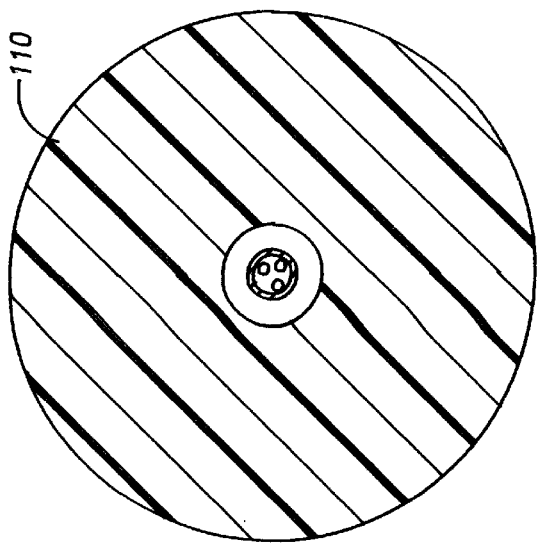

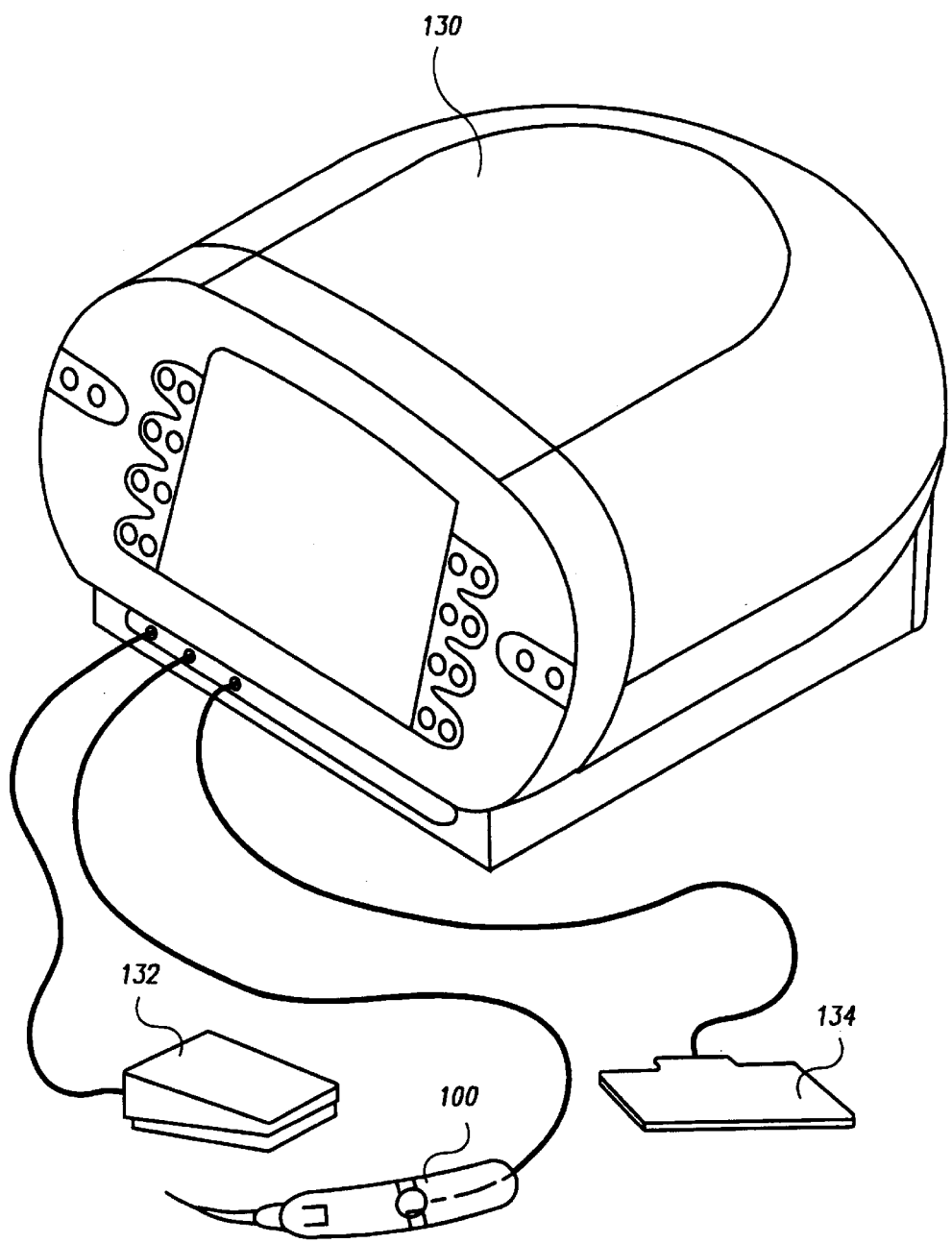
FIG.—1B

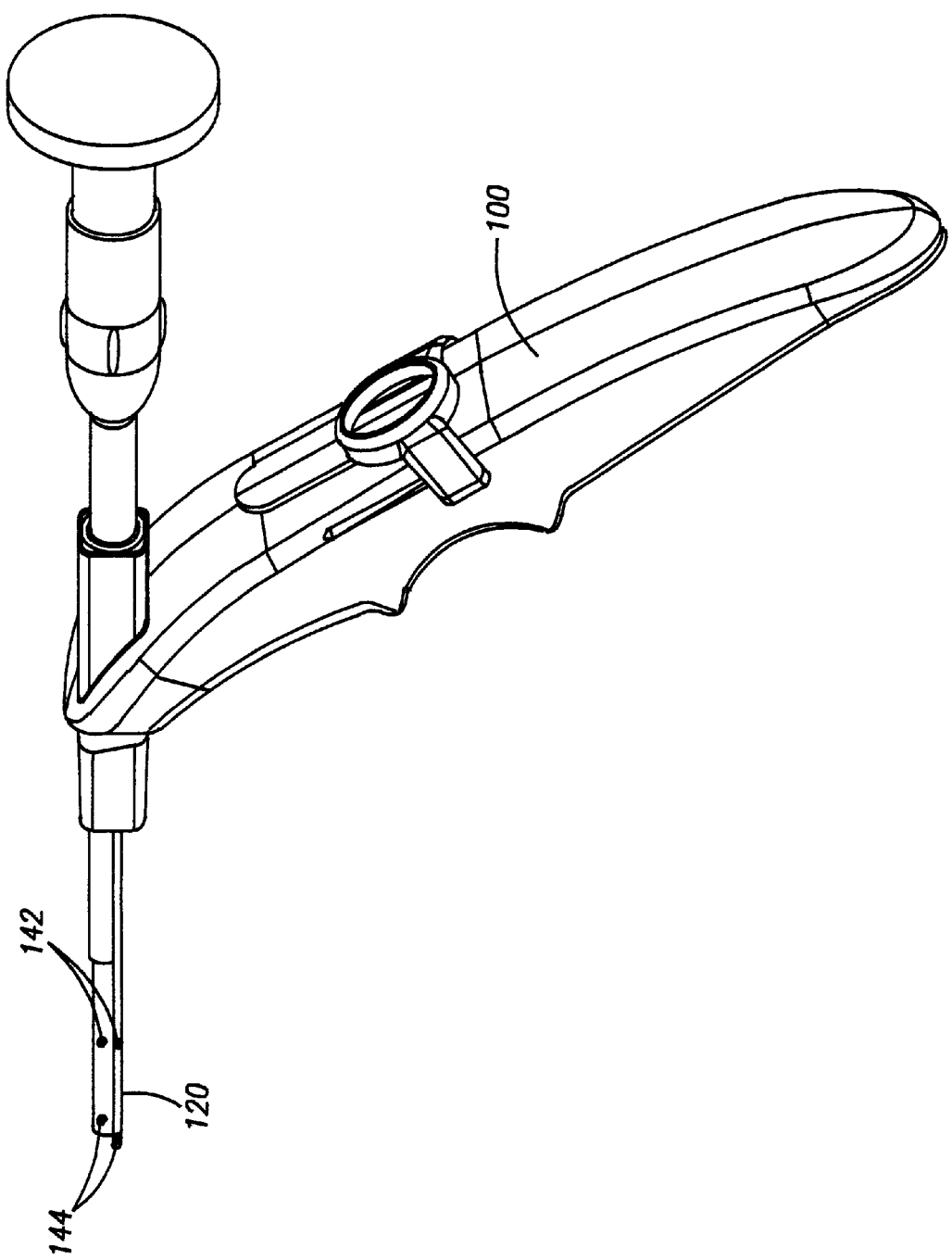

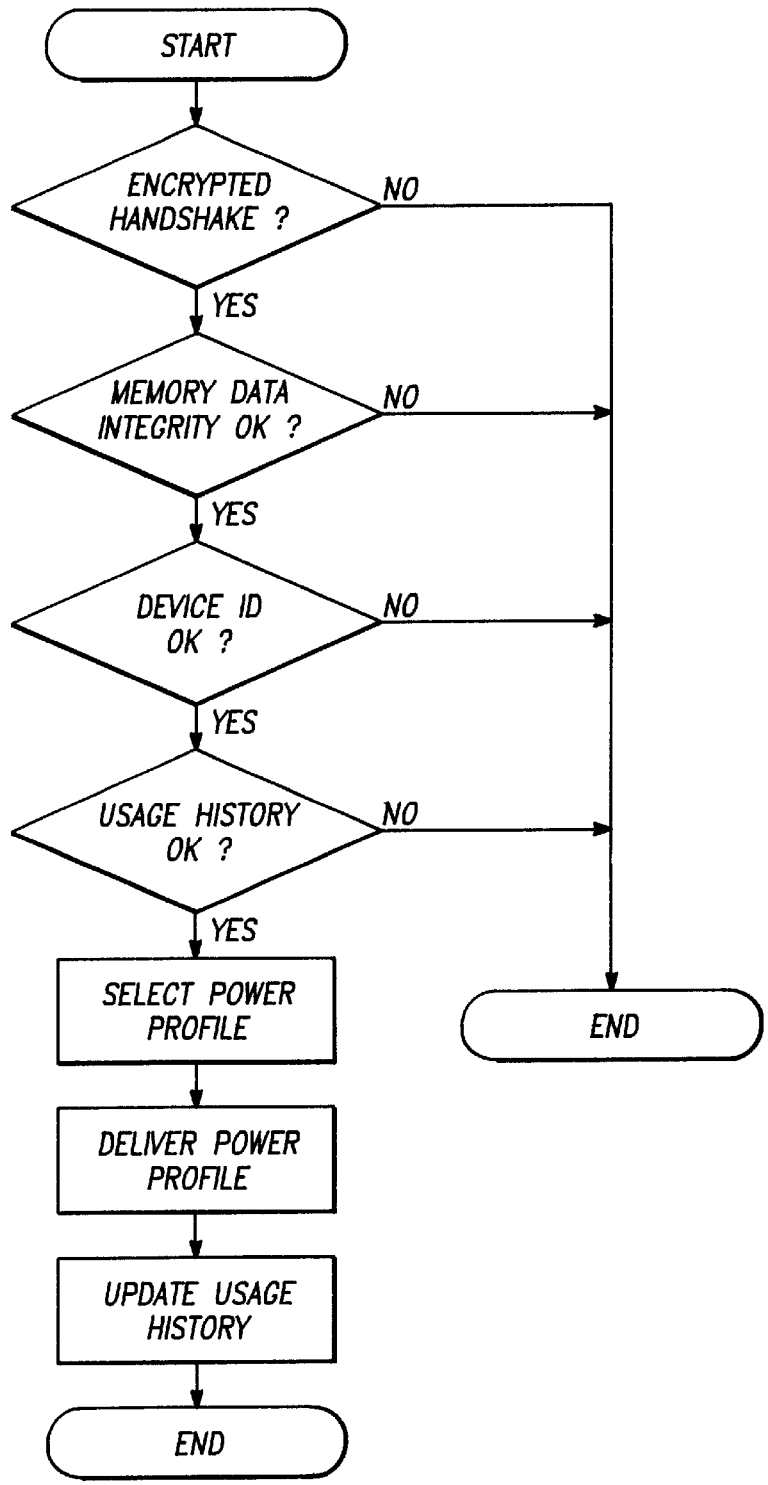
FIG.—3C

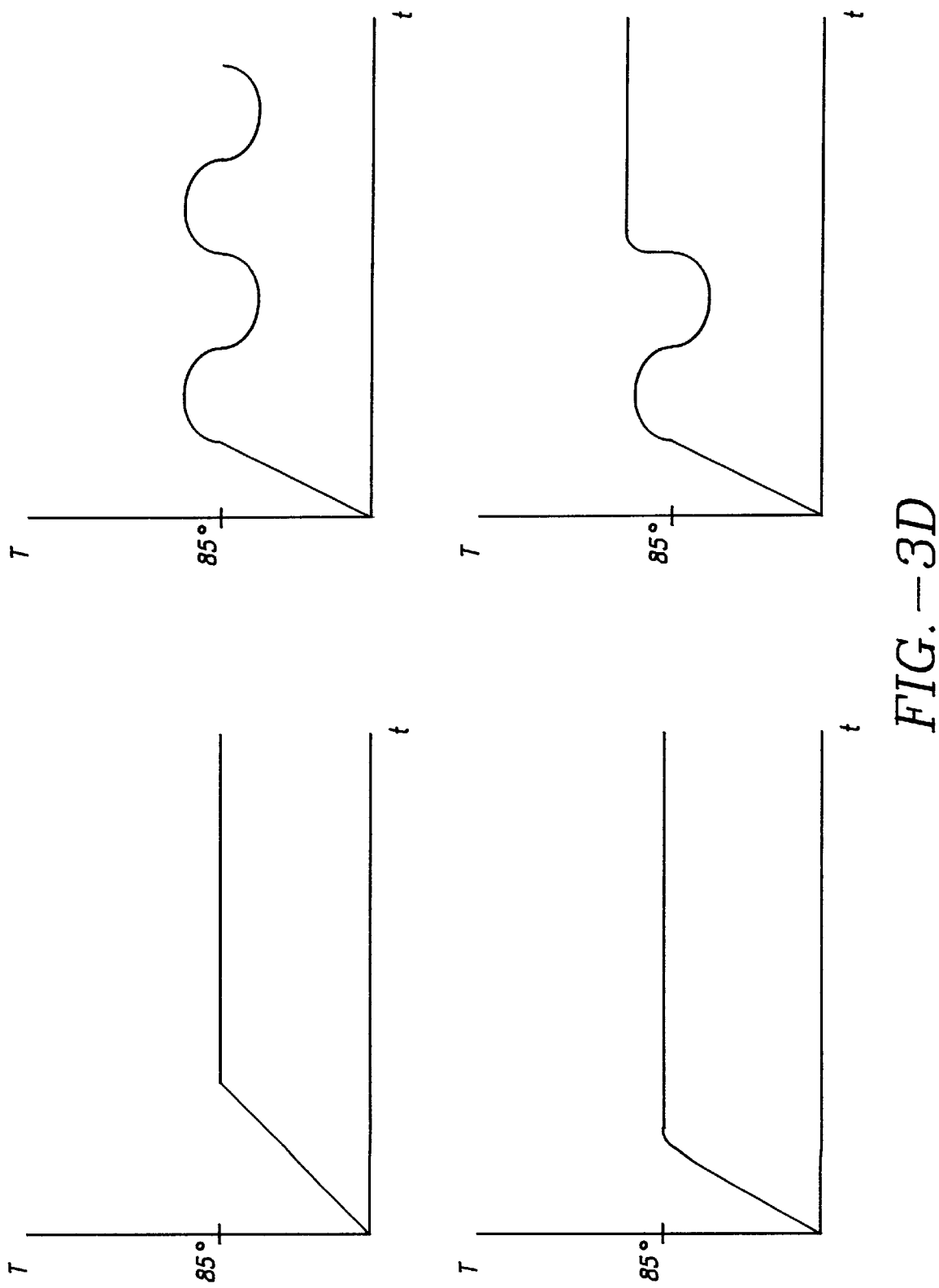
FIG.—3D

MEMORY FOR REGULATING DEVICE UTILIZATION AND BEHAVIOR

CROSS REFERENCE TO RELATED APPLICATIONS

This application claims the benefit of prior filed copending Provisional Application No. 60/061,197, filed on Oct. 6, 1997, entitled Memory for Regulating Device Utilization and Behavior, Provisional Application No. 60/062,458, filed on Oct. 6, 1997, entitled Linear Power Control With Digital Phase Lock, Provisional Application, Provisional No. 60/061,193, filed on Oct. 6, 1997, entitled Linear Power Control With PSK Regulation, Provisional Application No. 60/061,714, filed on Oct. 6, 1997, entitled Dual Processor Architecture For Electro Generator, Provisional Application No. 60/062,543, filed on Oct. 6, 1997, entitled Method And Apparatus For Power Measurement In Radio Frequency Electro-Surgical Generators, Provisional Application No. 60/061,213, filed on Oct. 6, 1997, entitled Method And Apparatus for Impedance Measurement In A Multi-Channel Electro-Surgical Generator, and U.S. application Ser.No. 08/912,273, filed on Aug. 15, 1997, entitled Apparatus And Device For Use Therein And Method For Ablation Of Tissue.

The present application is related to copending U.S. patent application Ser. No. 09/167,217, filed Oct. 6, 1998, entitled Linear Power Control With Digital Phase Lock, U.S. patent application Ser. No. 09/167412, filed Oct. 6, 1998, entitled Linear Power Control With PSK Regulation, U.S. patent application Ser. No. 09/167,508, filed Oct. 6, 1998, entitled Dual Processor Architecture For Electro Generator, U.S. patent application Ser. No. 09/167,505, filed Oct. 6, 1998, entitled Method And Apparatus For Power Measurement In Radio Frequency Electro-Surgical Generators, U.S. patent application Ser. No. 09/167,215, filed Oct. 6, 1998, entitled Method And Apparatus for Impedance Measurement In A Multi-Channel Electro-Surgical Generator, International Application No. PCT/US98/21065, filed Oct. 6, 1998, entitled Linear Power Control With Digital Phase Lock, and International Application No. PCT/US98/21066, filed October 1998, entitled Dual Processor Architecture For Electro Generator.

Each of the above-cited applications is incorporated herein by reference in its entirety.

BACKGROUND OF THE INVENTION

1. Field of the Invention

This invention relates to a cell necrosis apparatus. More particularly, this invention relates to a cell necrosis apparatus suitable for the treatment of tissue in the human body as for example the uvula, tonsils, adenoids, sinus tissue, tongue and turbinates.

2. Description of Related Art

Sleep-apnea syndrome is a medical condition characterized by daytime hypersomnolence, morning armaches, intellectual deterioration, cardiac arrhythmias, snoring and thrashing during sleep. It is caused by frequent episodes of apnea during the patient's sleep. The syndrome is classically subdivided into two types, One type, snoring and thrashing during sleep. It is caused by frequent episodes of apnea during effort. The second type, termed obstructive sleep apnea syndrome, is characterized by repeated apneic episodes during sleep resulting from obstruction of the patient's upper airway or that portion of the patient's respiratory tract which is cephalad to, and does not include, the larynx.

Treatment thus far includes various medical, surgical and physical measures. Medical measures include the use of medications such as protriptyline, medroxyprogesterone, acetazolamide, theophylline, nicotine and other medications in addition to avoidance of central nervous system depressants such as sedatives or alcohol. The medical measures above are sometimes helpful but are rarely completely effective. Further, the medications frequently have undesirable side effects.

Surgical interventions have included uvulopalatopharyngoplasty, tonsillectomy, surgery to correct severe retrognathia and tracheostomy. These procedures may be effective but the risk of surgery in these patients can be prohibitive and the procedures are often unacceptable to the patients.

Physical measures have included weight loss, nasopharyngeal airways, nasal CPAP and various tongue retaining devices used nocturnally. These measures may be partially effective but are cumbersome, uncomfortable and patients often will not continue to use these for prolonged periods of time. Weight loss may be effective but is rarely achieved by these patients.

In patients with central sleep apnea syndrome, phrenic nerve or diaphragmatic pacing has been used. Phrenic nerve or diaphragmatic pacing includes the use of electrical stimulation to regulate and control the patient's diaphragm which is innervated bilaterally by the phrenic nerves to assist or support ventilation. This pacing is disclosed in Direct Diaphragm Stimulation by J. Mugica et al. PACE vol. 10 January–February 1987, Part II, Preliminary Test of a Muscular Diaphragm Pacing System on Human Patients by J. Mugica et al. from Neurostimulation: An Overview 1985 pp. 263–279 and Electrical Activation of Respiration by Nochomovitez IEEE Eng. in Medicine and Biology; June, 1993.

However, it was found that many of these patients also have some degree of obstructive sleep apnea which worsens when the inspiratory force is augmented by the pacer. The ventilation induced by the activation of the diaphragm also collapses the upper airway upon inspiration and draws the patient's tongue anteriorly down the throat chocking the patient. These patients then require tracheostomies for adequate treatment.

A physiological laryngeal pacemaker as described in Physiological Laryngeal Pacemaker by F. Kaneko et al. from Trans Am Soc Artif Intern Organs 1985 senses volume displaced by the lungs and stimulates the appropriate nerve to open the patient's glottis to treat dyspnea. This apparatus is not effective for treatment of sleep apnea. The apparatus produces a signal proportional in the displaced air volume of the lungs and thereby the signal produced is too late to be used as an indicator for the treatment of sleep apnea. There is often no displaced air volume in sleep apnea due to obstruction.

One measure that is effective in obstructive sleep apnea is tracheostomy. However, this surgical intervention carries considerable morbidity and is aesthetically unacceptable to many patients. Other surgical procedures include pulling the tongue as forward as possible and surgically cutting and removing sections of the tongue and other structures which can close off the upper airway passage.

There is a need for an apparatus to treat air obstruction disorders that removes portions of the tongue and other airway structures without major surgical intervention.

SUMMARY OF THE INVENTION

The present invention is directed toward a cell necrosis apparatus, comprising: a housing having a proximal end and a distal end; an energy delivery device associated with the distal end of the housing, the energy delivery device capable of delivering an energy to a target tissue; an energy source connected to the energy delivery device, the energy source capable of controllably supplying the energy to the energy delivery device; and an identification and usage device coupled to the energy source, the identification and usage device capable of performing an encrypted handshake protocol with the energy source.

In another embodiment, a method is provided for creating cell necrosis in a body structure. A cell necrosis apparatus is provided and includes an energy delivery device as well as an identification and usage device. The cell necrosis apparatus undergoes an encrypted handshake protocol and an identification process. At least a portion of the energy delivery device is introduced into the body structure. Energy is delivered from the energy delivery device into the body structure to create cell necrosis.

BRIEF DESCRIPTION OF THE DRAWINGS

FIG. 1A shows one embodiment of a cell necrosis apparatus of the present invention.

FIG. 1B shows another embodiment of a cell necrosis apparatus of the present invention connected to an energy source.

FIG. 1C shows a cross-section view of one embodiment of the cell necrosis apparatus of the present invention.

FIG. 1D shows another cross-section view of one embodiment of the cell necrosis apparatus of the present invention.

FIG. 1E shows yet another embodiment of a cell necrosis apparatus of the present invention.

FIG. 2 shows a cross-section view of still yet another embodiment of the cell necrosis apparatus of the present invention having thermocouples.

FIG. 3C shows a flow process diagram of a method of device usage suitable for use with the identification and usage device of the present invention.

FIG.3D shows typical temperature control profiles which may be programmed into the identification and usage device of the present invention.

DETAILED DESCRIPTION

Figure 3A:
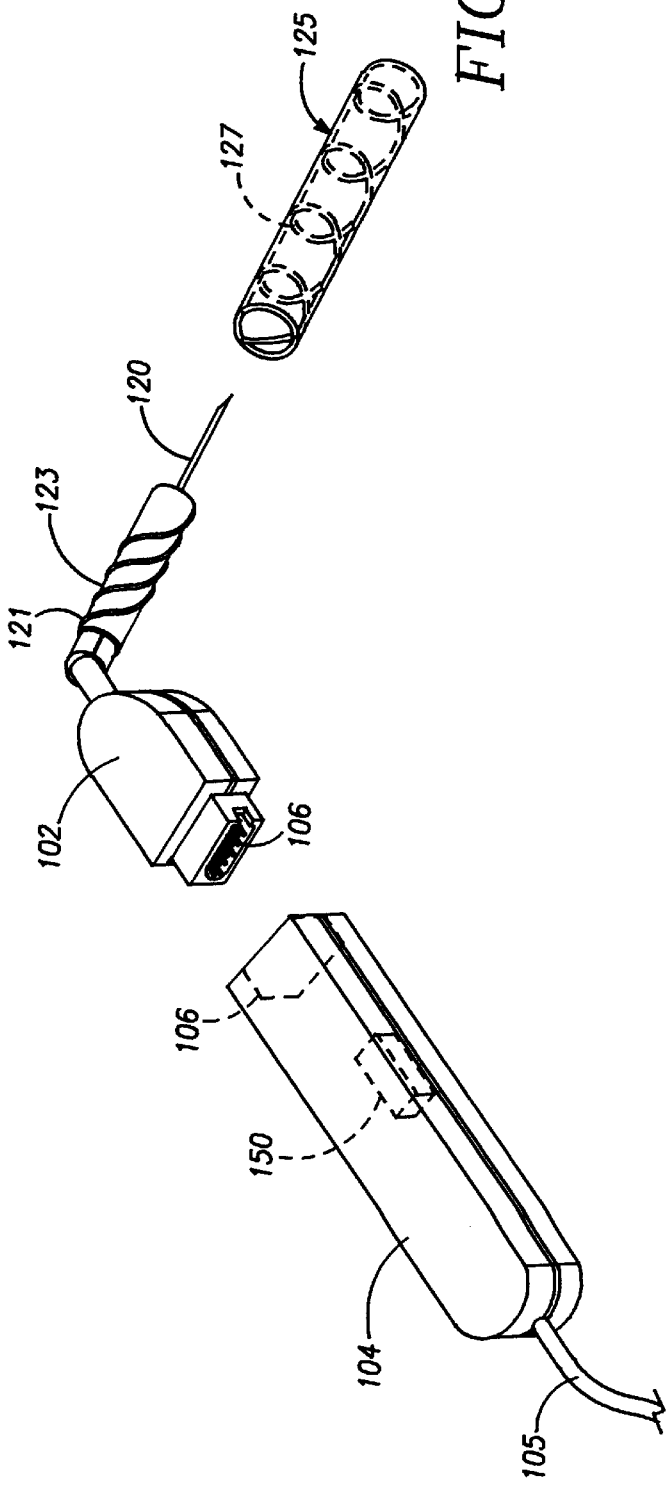
FIG. 3A shows one embodiment of the cell necrosis apparatus of the present invention having an identification and usage device.

FIG. 1A shows a cell necrosis apparatus 100 of the present invention. Cell necrosis apparatus 100 includes a housing 110 with a proximal end 112 and a distal end 114. Housing 110 may be formed of a suitable material such as a plastic.

Cell necrosis apparatus 100 also includes an energy delivery device 120 with a proximal end 122 and a distal end 124. Energy delivery device 120 may be selected to be of a suitable length and gauge according to the application. Energy delivery device 120 includes but is not limited to resistive heating, RF, microwave, coherent and incoherent light, ultrasound and liquid thermal jet. Energy delivery device 120 may be made of a suitable conductive material such as stainless steel which is capable of delivering an energy such as radiofrequency energy. Energy delivery device 120 may be completely uninsulated, or may be partially insulated with one or more insulating sleeves 121 of varying lengths and configurations to create a desired cell necrosis geometry.

Energy delivery device 120 may be removably attached to distal end 114 of housing 110 via a mounting device 116. Mounting device 1 16 is connected to an energy source 130. Mounting device 116 may be a standard Luer fitting which can accept off-the-shelf syringe needles. With such a mounting device 116, an off-the-shelf syringe needle may be used as an inexpensive and readily available energy delivery device 120, and may minimize a disposable portion of cell necrosis apparatus 100. Off-the-shelf syringe needles may also be readily modified by using heat-shrink tubing as insulating sleeves 121, cut to the desired size and fitted onto the syringe needles. One or more infusion ports may also be made in the sides of an off-the-shelf syringe needles.

FIG. 1B shows cell necrosis apparatus 100 connected to an energy source 130. Energy source 130 may include an automatic control device or a manual control device to control the amount of energy delivered. Energy source 130 may a separate standalone current that uses AC or DC current. Energy source 130 may include an activation device 132 and a grounding pad 134. Energy source 130 may deliver radiofrequency energy, ultrasound, microwave energy, or any other suitable energy.

FIG. 1C shows a longitudinal cross-section of another embodiment of cell necrosis apparatus 100. Here, cell necrosis apparatus 100 includes an energy delivery device 120 which is nonremovably attached to housing 110. In this configuration, proximal end 122 of energy delivery device 120 is mounted in a carrier 117 which is mounted within housing 110. FIG. 1D shows another cross-section of cell necrosis apparatus 100. FIG. 1E shows yet another embodiment of cell necrosis apparatus 100.

FIG. 2 shows cell necrosis apparatus 100 with feedback devices. These feedback devices may be adapted to be coupled to energy source 130 for sensing the application of radiofrequency energy as it is supplied by energy delivery device 120 to the tissue in the human body, and provide feedback for controlling the application of radiofrequency energy to the tissue. Feedback devices may include temperature sensing devices, such as first and second thermocouples 142 and 144. The first thermocouple 142 is mounted in distal end 114 of housing 110 and is provided for sensing the temperature of the tissue in the immediate vicinity of thermocouple 142 adjacent to an intermediate portion of energy delivery device 120 where it enters housing 110. The second thermocouple 144 is mounted in distal end 124 of energy delivery device 120 and senses the temperature of the tissue in the immediate vicinity of distal end 124 of energy delivery device 120.

Cell necrosis apparatus 100 may be briefly described as follows. Assuming that cell necrosis apparatus 100 has been connected to energy source 130, the user may grasp housing 110 of the device by the fingers of a hand or in the palm of the hand and with a straight energy delivery device 120 as shown in FIG. 1, the user can utilize housing 110 to cause energy delivery device 120 to penetrate the tissue or cells it is desired to necrose. Energy delivery device 120 may be positioned so that insulating sleeve 121 engaging proximal end 122 of energy delivery device 120 is well past the mucosal layers of the tissue, after which energy source 130 can be turned on. This ensures that the mucosal layer will remain undamaged and will not be thermally necrosed.

Energy delivery device 120 can be utilized as a unipolar device with a grounding pad (not shown) being provided on the patient as for example on the back of the patient to complete the circuit for a radiofrequency energy from the power supply and the return to the power supply. For example, with a straight energy delivery device 120, the turbinates can be readily treated with cell necrosis apparatus 100. The treatment can be carried out for an appropriate length of time from 20 seconds to 5 minutes with a radiofrequency energy being applied at a desired frequency, as for example a frequency of 580 kHz and a power level ranging from 5 to 50 W. The shorter times are desirable where the size of the anatomical feature to be treated is small (such as the uvula) or where the tissue is highly hydrated or perfused. This helps to preserve anatomical tissue in the region to be necrosed, as for example anatomical features which are then in cross-section (i.e., mucosal membranes). Feedback devices such as thermocouples 142 and 144 may be utilized for automatically terminating the application of radiofrequency power when a certain temperature in the tissue has been reached as sensed by either one or both of thermocouples 142 and 144. The delivery of radiofrequency energy to energy delivery device 120 is terminated before energy delivery device 120 is withdrawn from the tissue to avoid surface layer thermal damage. After the procedure has been completed, the physician can withdraw cell necrosis apparatus 100 and can further proceed with the procedure by inserting energy delivery device 120 of cell necrosis apparatus 100 into another location using the same procedure. The foregoing steps can be repeated as necessary to complete the desired necrosis of the tissue being treated.

In the case of some smaller anatomical features, the physician may use lower power levels to obtain a lesion of sufficient size without premature desiccation of the tissue surrounding energy delivery device 120. This lower rate of energy delivery is an important aspect of the present invention because it yields larger lesions and greater volume per penetration than would occur if the power settings were higher. In that case, rapid heating can result in loss of current delivery due to tissue desiccation. The reason the lower power settings result in larger lesions is that the hydrated tissue exhibits thermal conductivity at a fairly inefficient level, but is nonetheless somewhat thermally conductive. If the power setting is appropriate, the tissue is able to conduct the energy outwardly in the form of heat and the tissue immediately adjacent to energy delivery device 120 will be kept below the temperature of vaporization of the fluid within the tissue. When vaporization occurs, there is a fluctuation of the ohmic impedance to current flow and the tissue rapidly desiccates, resulting in interruption of the circuit. This loss of current flow due to overheating of the tissue adjacent to energy delivery device 120 can be an advantage in that it is a safety aspect of the present invention. For instance, in the event of inadvertent setting of the power at a high level, the rapid desiccation of the thin layer of cells in contact with the active electrode will break the circuit and act as a "biologic switch", cutting off current flow and preventing extensive tissue damage. Only by setting the power at lower levels, as for example 1 W, can larger lesions be attained. Power settings up to 15 W may be used with energy delivery device 120. Situations where power levels as high as 50 or 100 W can occur where an energy delivery device 100 with a significantly larger surface area is used or where the tissue is highly perfused and the circulatory (blood flow) rate is high, resulting in efficient cooling of the tissue being treated.

For performing other tissue ablation procedures where a curved or bent energy delivery device 120 is desired, energy delivery device 120 may be formed of a malleable material and can be bent in a suitable manner to the desired configuration to match the anatomy, as for example the treatment of soft palate, tonsils, adenoids and sinus tissue. A straight needle may be utilized for treating the uvula.

After the device has been used, it can be disposed of because the device has been designed for a one time use even though the device is manufactured in such a way that it is sterilizable. However, sterilizing the same may be undesirable when it is difficult to ensure that sufficient sterilization has been accomplished and particularly if blood has coagulated on energy delivery device 120 causing a protein buildup which may not be removed during the sterilization procedure. It should be appreciated as hereinbefore explained that the device can still be further simplified by using only one thermocouple. It is possible to utilize only one thermocouple by estimating the temperature gradient which normally occurs between a first and second thermocouples. By utilizing only one thermocouple it is possible to go to a solid wire for energy delivery device 120 rather than a needle which has a lumen or bore therein.

FIG. 3A shows one embodiment of cell necrosis apparatus 100 having an identification and usage device 150. Energy delivery device 120 is inclined at an angle with respect to the central axis of housing 110 as for example at an angle of 45°. An insulating sleeve 121 is provided on the needle and has a length so that the exposed end of energy delivery device 120 extends for a length according to the application and preferences of the user. In this embodiment, insulating sleeve 121 is provided with threads 123 on its exterior surface. Threads 123 may be relatively coarse, as for example a quarter pitch, so that a protective sleeve 125 with threads 127 on its interior surface matching threads 123 can be threaded on and off of insulating sleeve 121 with four to five turns of protective sleeve 125. Protective sleeve 125 may be formed of a suitable material such as plastic. Protective sleeve 125 has a length so that it will extend over the length of insulating sleeve 121 and still provide adequate space for energy delivery device 120 to extend distally from insulating sleeve 121. This threaded arrangement is preferable to one which is mounted by a slip fit because a slip fit requires movement of the sleeve towards and away from the needle during pushing and pulling of the sleeve, making it possible for the physician using the same to inadvertently be punctured by energy delivery device 120.

After cell necrosis apparatus 100 has been used, a disposable portion 102 can be separated from a reusable portion 104 and only disposable portion 102 disposed of after use. Reusable portion 104 with a cable 105 can be retained for future reuse. Reusable portion 104 can be readily sterilized if necessary and carries the carrier components which are often the major expense in fabricating housing 110. Thus it can be seen that such a design makes it possible to further reduce the cost of cell necrosis apparatus 100.

Figure 3B:
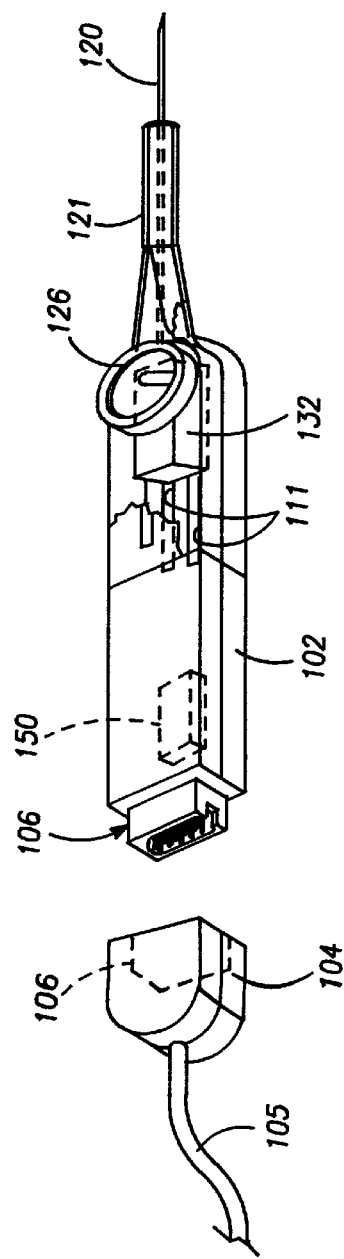
FIG. 3B shows another embodiment of the cell necrosis apparatus of the present invention having an identification and usage device.

FIG. 3B shows another embodiment of cell necrosis apparatus 100 having an identification and usage device 150. Housing 110 has disposable and reusable portions 102 and 104. A connector assembly 106 is provided for coupling disposable and reusable portions 102 and 104 and the wires or conductors utilized in cell necrosis apparatus 100.

In this embodiment, energy delivery device 120 is carried by housing 110 and is coupled to a slider 132 which is slidably mounted in guides 111 within housing 110. Energy delivery device 120 thus may be moved between a fully extended position where energy delivery device 120 extends beyond insulation sleeve 121 forming a part of housing 110, and a fully retracted position in which energy delivery device 110 is completely retracted within insulation sleeve 121. Slider 132 is coupled to and under the control of a knob 126 slidably mounted on the exterior of housing 110 and adapted to be grasped by a finger of the hand and particularly the thumb of the hand holding cell necrosis apparatus 100. Knob 126 may have a centrally disposed recess adapted to be engaged by the thumb of the holding hand. Folded wires or conductors (not shown) permit the slider 132 to move between extended and retracted positions while still continuing to receive information from any feedback devices and to supply an energy to energy delivery device 120.

With the retractable energy delivery device 100, it is possible for the physician to position energy delivery device 100 in the desired position merely by engaging knob 126 by the thumb of the hand while the same hand is holding cell necrosis apparatus 100 to advance energy delivery device 120 into the tissue to be treated. After the application of radiofrequency energy, energy delivery device 120 can be retracted back into housing 110 without danger of the physician being pricked by energy delivery device 120. Part of energy delivery device 100 can still be reused by separating proximal portion 112 which carries the cable 41 from distal portion 114 so that distal portion 114 can be disposed of after a one-time use.

Identification and usage device 150 prevents pirating of cell necrosis apparatus 100 by outside vendors and recording of repeated use of the cell necrosis apparatus 100. Identification and usage device 150 may be an EEPROM or other suitable device. Identification and usage device 150 may be housed within housing 110. Identification and usage device 150 is connected to an energy source 130 which can recognize, utilize, and/or be controlled by identification and usage device 150. Identification and usage device 150 may also be connected to any feedback devices and energy delivery device 120. Identification and usage device 150 may be a non-volatile memory device such as EEPROM, non-volatile RAM, flash memory, magnetic data storage device, or optical data storage device.

Identification and usage device 150 may include identification data such as manufacturer, model number, serial number, and date of manufacture. Energy source 130 may be programmed to recognize and accept only a cell necrosis apparatus 100 that is compatible or has been authorized for use with energy source 130. Energy source 130 may also have a data integrity check procedure, in which identification and usage device 150 undergoes a checksum or CRC process to check the integrity of the data stored on identification and usage device 150. Identification and usage device 150 may be programmed with an encrypted handshake protocol which positively establishes a connection between identification and usage device 150 and energy source 130. This encrypted handshake protocol serves to prevent the use of unauthorized or pirated cell necrosis apparatus 100, and discourages attempts to defeat the objectives of the non-volatile memory system.

Identification and usage device 150 may also be programmed with parametric information which can inform energy source 130 what type of cell necrosis apparatus 100 is being connected. Energy source 130 may include a database of different types and kinds of devices, so that identification information will allow energy source 130 to adjust its output according to the particular device connected. Alternatively, identification and usage device 150 may provide its own parametric data such as voltage limits, current limits, instrument impedance, voltage setpoints, current setpoints, voltage ranges, current ranges, scale factors, number of channels, number of thermocouples, and thermocouple insulation configuration.

Identification and usage device 150 may cause a record to be made of each use of cell necrosis apparatus 100. This record of use may be in the form of "flight recorder" style data including time and date of use, length of use, number of uses, amount of energy delivered, and other use-related data. This detailed data permits diagnostics to be performed on the equipment, as well as allows post-treatment verification that the equipment had been properly used. "Flight recorder" style data may be stored in identification and usage device 150 at predetermined intervals, for example, every 5 seconds. If cell necrosis apparatus 100 is used inappropriately, energy source 130 may be programmed to shut off. For example, if cell necrosis apparatus 100 is used for too long, a warning may be given to the user before cell necrosis apparatus 100 automatically ceases to operate. As another example, if a preset amount of time has elapsed since the last use, the user may be advised to sterilize cell necrosis apparatus 100 before use.

FIG. 3C shows a flowchart of one embodiment of the decision process of energy source 130. When energy source 130 is connected to cell necrosis apparatus 100, energy source 130 and identification and usage device 150 undergo an encrypted handshake protocol, data integrity check, device identification process, and a usage history check. If any of these processes are not successfully completed, then energy source 130 will not deliver any power to cell necrosis apparatus 100. Otherwise, energy source 130 will begin the power profile selection and power delivery processes, and update the usage history.

FIG. 3D shows graphs of temperature versus time for some typical temperature control profiles which may be programmed into identification and usage device 150. By controlling the rate at which the temperature of the tissue increases at the beginning of the treatment, a more uniform necrosis can be achieved and excessive thermal damage avoided. Various patterns such as a cyclical temperature profile or a temperature profile with a single peak may be programmed into the microprocessor, as opposed to a single constant temperature.

An effective and appropriate amount of energy delivered by energy source 130 to cell necrosis apparatus 100 can be selected depending upon the tissue to be necrosed and data from the feedback devices. For example, turbinate tissue can be given 350 J, palate tissue can be given 500 J, and tongue tissue can be given 1000 J. Thermocouples 142 and 144 can measure the temperature of the tissue being necrosed, which is dependent of the amount of energy being applied as well as the heat transfer characteristics of the tissue being necrosed.

In one embodiment of the present invention a method is provided for creating cell necrosis in a body structure. Suitable body structures include but are not limited to the tonsils, uvula, soft palate, turbinates, tongue and the like. A cell necrosis apparatus 100 is provided and includes an energy delivery device 120 as well as an identification and usage device 150. Cell necrosis apparatus 100 undergoes an encrypted handshake protocol and an identification process. At least a portion of the energy delivery device is introduced into the body structure. Energy is delivered from the energy delivery device into the body structure to create cell necrosis.

EXAMPLE

Figure 3E:
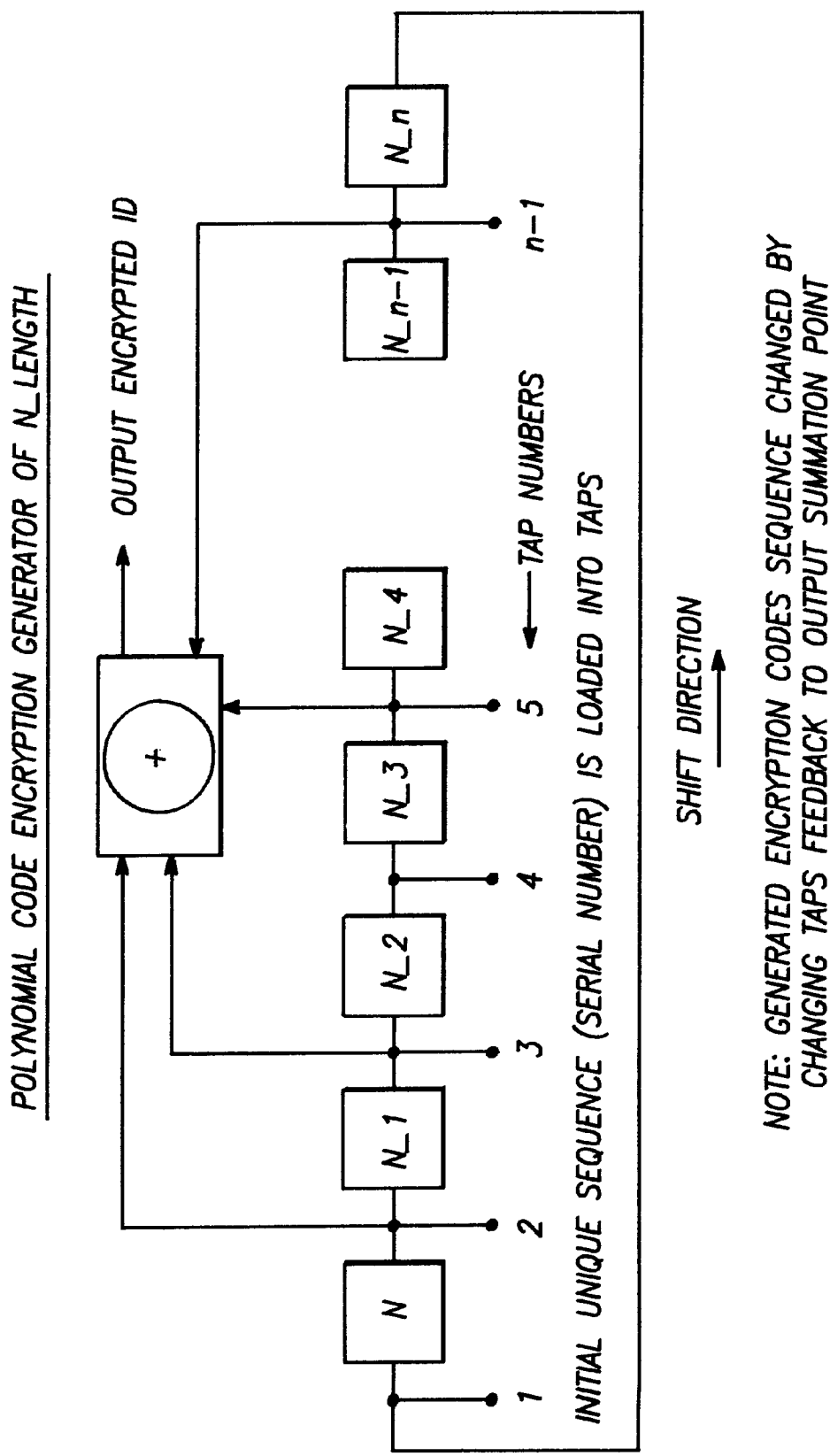
FIG. 3E shows a graphical representation of a polynomial code encryption generator suitable for use with the identification and usage device of the present invention.

Embedded in identification and usage device 150 is unique ID used to identify cell necrosis apparatus 100 to energy source 130. A unique n-length bit binary number (serial number) may be used as a seed for a pseudorandom number generator. The pseudorandom number generator is incremented a known number of times to generate another n-length bit binary number. FIG. 3E shows an example of a polynomial code encryption generator of N-length which may be used to generate pseudorandom numbers. One method of generating pseudorandom numbers includes loading an initial unique sequence, such as the serial number, into taps 302. A generated encryption codes sequence is changed by changing taps feedback to an output summation point 304, such as by shifting in a shift direction. The output summation point generates the output encrypted identification code.

Figure 3F:
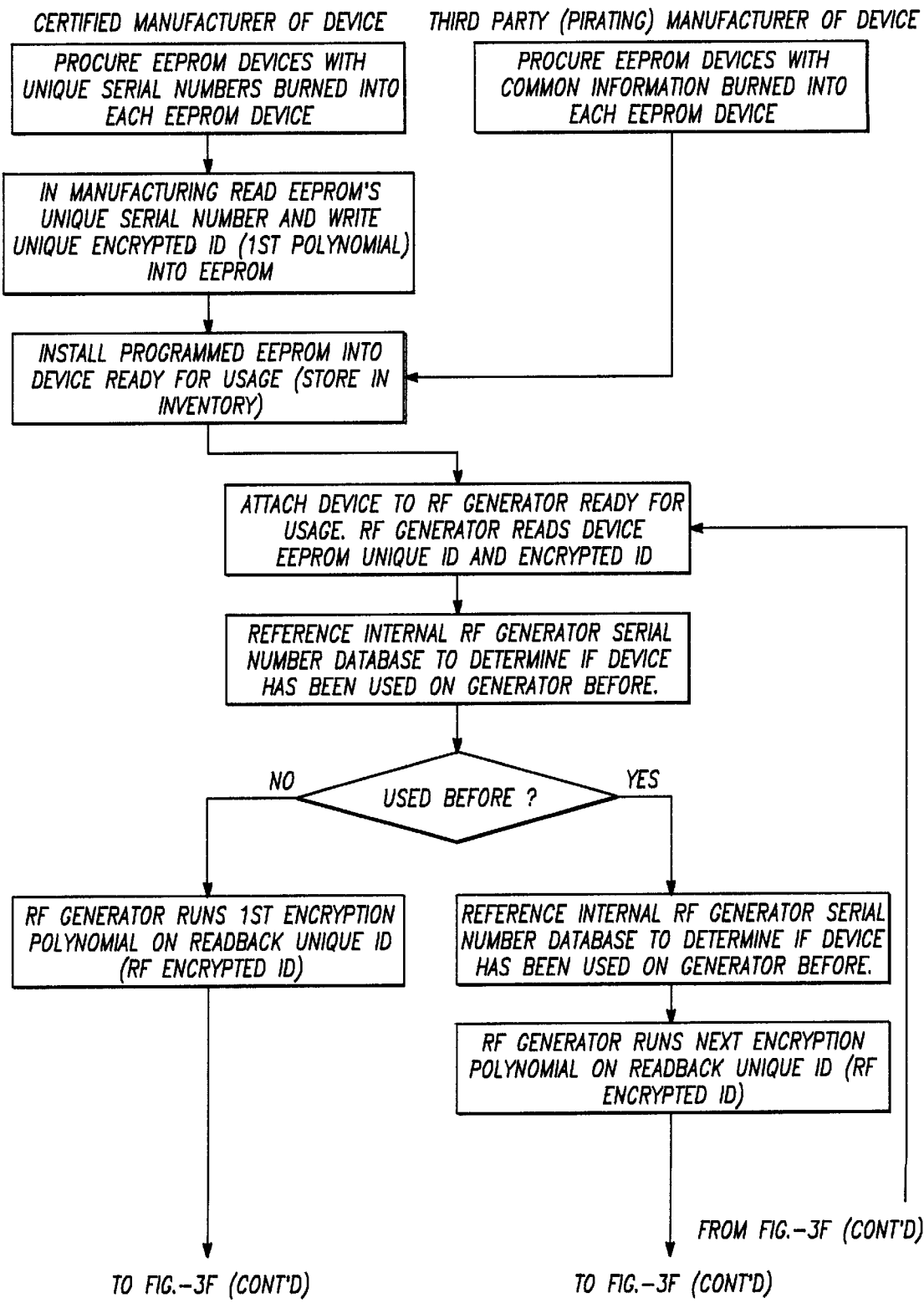
FIG. 3F shows a flow process diagram for a verification process suitable for use with the identification and usage device of the present invention.
Figure 3F:
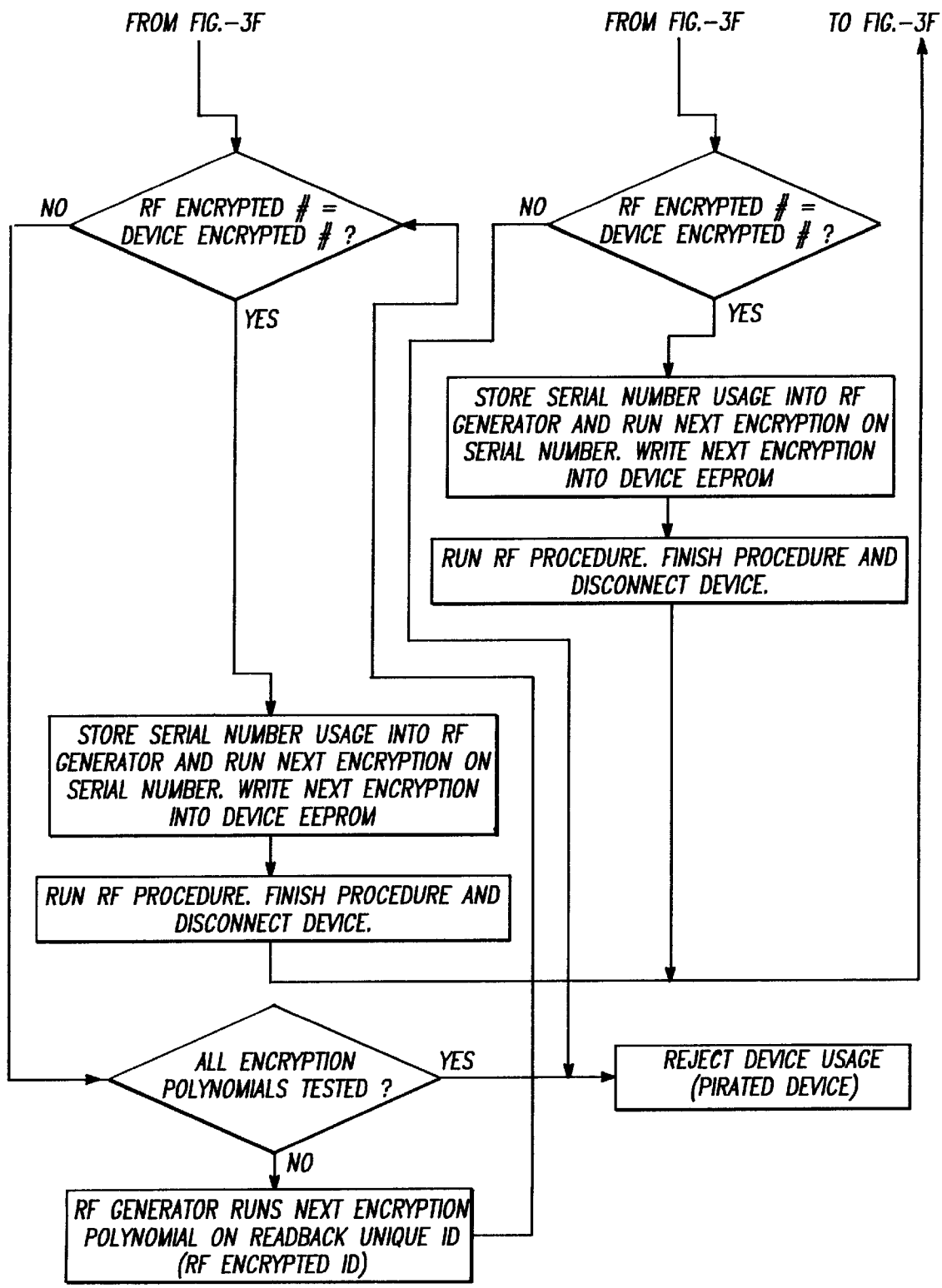

Both of these numbers are stored in known locations in identification and usage device 150 in cell necrosis apparatus 100. When cell necrosis apparatus 100 is connected to energy source 130, energy source 130 reads the unique ID and encrypted ID. Energy source 130 then encrypts the unique ID and then compares it to the encrypted ID stored in identification and usage device 150. If both the encrypted IDs are the same, cell necrosis apparatus 100 is accepted and the protocol is permitted to begin. If the IDs do not match, energy source 130 will not permit the usage of the connected device. At this point, energy source 130 uses the unique ID to generate a new encrypted ID. Energy source 130 overwrites the first encrypted ID in identification and usage device 150 with the newly generated encrypted ID. Each time cell necrosis apparatus 100 is used on energy source 130, a new pseudo random number generator is used to generate a unique encrypted ID for the device. FIG. 3F shows a flow chart of one example of this verification process which prevents third party vendors from mimicking a certified manufacturers device. This example uses an RF generator as energy source 130 and an EEPROM as identification and usage device 150.

Energy source 130 may limit the use of cell necrosis apparatus 100 by using logic based on reading and writing information to identification and usage device 150. Identification and usage device 150 may come from the factory with three stored parameters to control use: time parameters $D_1$ and $D_2$ and maximum joules parameter $J_M$. Energy source 130 may limit use of cell necrosis apparatus 100 by writing the date and time of initial energy delivery and by updating accumulated joules delivered to cell necrosis apparatus 100 in identification and usage device 150. $D_1$ will set the duration (clock time; independent of energy delivery time) from initial energy delivery until an audible tone and a warning message such as: "Device designed for single use only . . . the device will be disabled in XX minutes." This warning message and tone will occur when the ready state is entered following the $D_1$ interval. The warning message will display the time remaining until cell necrosis apparatus 100 is disabled. $D_2$ will set the duration from initial energy delivery until energy delivery ceases to function with cell necrosis apparatus 100.

If $D_1$ is set to zero, no warning message appears and cell necrosis apparatus 100 shuts down after the duration set by $D_2$. If $D_2$ is set to zero then no shut off is activated. If $D_1$ and $D_2$ are set to zero then no duration based control of use function is activated.

Energy source 130 may also shut down energy delivery if accumulated joules delivered ($J_D$) to cell necrosis apparatus 100 exceeds the maximum joules ($J_M$) stored in identification and usage device 150. A warning message and tone will occur each time the ready state is entered once the accumulated joules delivered ($J_D$) exceeds the maximum joules ($J_M$) stored in identification and usage device 150. A warning message will also occur when entering the ready state when less than 15% or other percentage of total joules are remaining. This message will state the joules remaining in the counter. If $J_M$ is set to zero than no joules based control of use will be activated. In no case will energy delivery be interrupted by the control of use function.

Identification and usage device 150 may contain a parameter for mode ($M_1$). $M_1$ may describe the number of needles, number of thermocouples, and mapping of pin-outs in the device. Energy source 130 may configure itself according to the mode contained in identification and usage device 150. Energy source 130 may display the mode and also check for the corresponding active thermocouples. Identification and usage device 150 may also contain procedural set up parameters. For example, $T_1$ may set target temperature, $J_1$ may set target joules, $P_1$ may set maximum power, and $I_M$ may set maximum impedance threshold.

A power delivery profile may be established by certain parameters contained in identification and usage device 150. If parameters are not set then a default profile may be called. Profile parameters may include $A_1$ (ramp increment) and $A_2$ (ramp slope at onset based on actual temperature compared to target) and $A_3$ (ramp slope past onset based on actual temperature compared to target). This allows variations in ramp speed and ramp profile.

Identification and usage device 150 may also contain a patented design or trademark called $L_1$ which acts as a competitive lockout. The competitive lockout will prohibit the use of devices which do not contain an identification and usage device 150.

Energy source 130 may write to cell necrosis apparatus 100 during use to set or increment certain use information. This may include date/time of first use, date/time of last use, total joules delivered, total energy delivery time, maximum impedance during energy delivery, maximum tip temperature, maximum insulation temperature, generator error codes, and number of times $D_1$ message was initiated if $D_2$ was activated.

From the foregoing it can be seen that there has been provided an apparatus which can be utilized for cell necrosis in connection with energy source. The devices are small and adapted to be held by the human hand and are designed in such a manner so that the entire device or only a portion of the device can be disposed of after a one-time use. Static or retractable needles can be provided. The construction has been kept so that it is relatively simple to minimize the cost of construction and inexpensive materials have been utilized where possible.

What is claimed is:

1. A cell necrosis apparatus, comprising:
  a housing having a proximal end and a distal end;
  an energy delivery device associated with the distal end of the housing, the energy delivery device capable of delivering an energy to a target tissue;
  an energy source connected to the energy delivery device, the energy source capable of controllably supplying the energy to the energy delivery device; and
  an identification and usage device associated with the energy source and the energy delivery device, the identification and usage device capable of performing an encrypted handshake protocol with the energy source.

2. The device of claim 1, wherein the identification and usage device is capable of storing data associated with a tissue device.

3. The device of claim 2, wherein the data includes parametric information associated with the cell necrosis apparatus.

4. The device of claim 3, wherein the parametric information includes a particular configuration of the cell necrosis apparatus.

5. The device of claim 3, wherein the parametric information includes at least one temperature control profile.

6. The device of claim 5, wherein the temperature control profile is selected according to the cells to be necrosed.

7. The device of claim 2, wherein the data includes a usage history associated with the cell necrosis apparatus.

8. The device of claim 7, wherein the usage history includes a time and date of a use.

9. The device of claim 7, wherein the usage history includes an amount of energy delivered.

10. The device of claim 7, wherein the usage history includes feedback data from at least one feedback device.

11. A cell necrosis apparatus, comprising:
a housing having a proximal end and a distal end, the housing having an identification and usage device coupled to an energy source, the identification and usage device performing an encrypted handshake protocol with the energy source; and
an energy delivery device associated with the distal end of the housing, the energy delivery device capable of being connected to the energy source and delivering an energy to a target tissue.

12. The device of claim 11, wherein the identification and usage device is capable of storing data associated with a tissue device.

13. The device of claim 12, wherein the data includes parametric information associated with the cell necrosis apparatus.

14. The device of claim 13, wherein the parametric information includes a particular configuration of the cell necrosis apparatus.

15. The device of claim 13, wherein the parametric information includes at least one temperature control profile.

16. The device of claim 15, wherein the temperature control profile is selected according to the cells to be necrosed.

17. The device of claim 12, wherein the data includes a usage history associated with the cell necrosis apparatus.

18. The device of claim 17, wherein the usage history includes a time and date of a use.

19. The device of claim 17, wherein the usage history includes an amount of energy delivered.

20. The device of claim 17, wherein the usage history includes feedback data from at least one feedback device.

* * * * *